United States Patent
Evangelista

(10) Patent No.: US 8,168,230 B2
(45) Date of Patent: May 1, 2012

(54) PLATELET GEL COMPRISING PLATELET-RICH PLASMA, PLATELET ACTIVATOR AND POLYMER

(75) Inventor: Virgilio Evangelista, Fossacesia (IT)

(73) Assignee: Advance Holdings Limited, Floriana (MT)

( * ) Notice: Subject to any disclaimer, the term of this patent is extended or adjusted under 35 U.S.C. 154(b) by 1535 days.

(21) Appl. No.: 11/313,781

(22) Filed: Dec. 22, 2005

(65) Prior Publication Data

US 2006/0140923 A1 Jun. 29, 2006

(30) Foreign Application Priority Data

Dec. 24, 2004 (IT) .............................. RM2004A0638

(51) Int. Cl.
- *A61K 35/14* (2006.01)
- *A61K 9/00* (2006.01)
- *A01N 63/00* (2006.01)
- *A61F 2/00* (2006.01)

(52) U.S. Cl. ..................... 424/532; 424/93.72; 424/400; 424/423

(58) Field of Classification Search ......................... None
See application file for complete search history.

(56) References Cited

U.S. PATENT DOCUMENTS

| | | | |
|---|---|---|---|
| 5,834,418 | A | 11/1998 | Brazeau et al. |
| 6,322,785 | B1 | 11/2001 | Landesberg et al. |
| 6,398,972 | B1 | 6/2002 | Blasetti et al. |
| 6,524,568 | B2 | 2/2003 | Worden |
| 7,074,765 | B2 * | 7/2006 | Schmaier et al. ............... 514/12 |
| 2003/0152639 | A1 | 8/2003 | Britton et al. |
| 2004/0197319 | A1 | 10/2004 | Harch et al. |

FOREIGN PATENT DOCUMENTS

| | | |
|---|---|---|
| GB | 495675 | 11/1938 |
| WO | WO 02/00272 A2 | 1/2002 |
| WO | WO 02/080991 A2 | 10/2002 |
| WO | WO 2004/024180 A1 | 3/2004 |

OTHER PUBLICATIONS

Dean H. Whitman, et al., "Platelet Gel: An Autologous Alternative to Fibrin Glue With Applications in Oral and Maxillofacial Surgery", J. Oral Maxillofacial Surgery, vol. 55, 1997, pp. 1294-1299.
Robert E. Marx, et al., "Platelet-rich plasma, Growth factor enhancement for bone grafts", Oral Surgery, Oral Medicine, Oral Pathology, Oral Radiol., Endod., vol. 85, No. 6, Jun. 1998, pp. 638-646.
Shaun R. Coughlin, "Thrombin signalling and protease-activated receptors", Nature, www.nature.com, vol. 407, Sep. 14, 2000, pp. 258-264.
Claudia K. Derian, et al., "Design and Evaluation of Potent Peptide-Mimetic $PAR_1$ Antagonists", Drug Development Research, vol. 59, 2003, pp. 355-366.
E. Sumida, et al., "1207 Preparation of Platelet-Rich Plasma (PRP) Without Centrifugation", http://iadr.confex.com, $82^{nd}$ General Session, Mar. 10-13, 2004, 1 page.

* cited by examiner

*Primary Examiner* — David Naff
(74) *Attorney, Agent, or Firm* — Oblon, Spivak, McClelland, Maier & Neustadt, L.L.P.

(57) ABSTRACT

A semi-synthetic platelet gel comprising a platelet-rich plasma, at least one platelet activator, and a biocompatible polymer selected from the group comprising carbomers, polyalkylene glycols, poloxamers, polyesters, polyethers, polyanhydrides, polyacrylates, polyvinyl acetates, polyvinyl pyrrolidones, polysaccharides, and derivatives thereof. A method for preparing a semi-synthetic platelet gel comprising the steps of (a) mixing a platelet-rich plasma with at least one platelet activator, and, before the start of clot formation, (b) adding the mixture thus obtained to a biocompatible polymer selected from the group comprising carbomers, polyalkylene glycols, poloxamers, polyesters, polyethers, polyanhydrides, polyacrylates, polyvinyl acetates, polyvinyl pyrrolidones, polysaccharides, and derivatives thereof.

14 Claims, No Drawings

SEQUENCE LISTING

<160> NUMBER OF SEQ ID NOS: 4

<210> SEQ ID NO 1
<211> LENGTH: 6
<212> TYPE: PRT
<213> ORGANISM: ARTIFICIAL
<220> FEATURE:
<223> OTHER INFORMATION: TRAP protein sequence

<400> SEQUENCE: 1

Ser Phe Leu Leu Arg Asn
1               5

<210> SEQ ID NO 2
<211> LENGTH: 5
<212> TYPE: PRT
<213> ORGANISM: ARTIFICIAL
<220> FEATURE:
<223> OTHER INFORMATION: TRAP-5

<400> SEQUENCE: 2

Ser Phe Leu Leu Arg
1               5

<210> SEQ ID NO 3
<211> LENGTH: 7
<212> TYPE: PRT
<213> ORGANISM: ARTIFICIAL
<220> FEATURE:
<223> OTHER INFORMATION: TRAP-7

<400> SEQUENCE: 3

Ser Phe Leu Leu Arg Asn Pro
1               5

<210> SEQ ID NO 4
<211> LENGTH: 14
<212> TYPE: PRT
<213> ORGANISM: ARTIFICIAL
<220> FEATURE:
<223> OTHER INFORMATION: TRAP-15

<400> SEQUENCE: 4

Ser Phe Leu Leu Arg Asn Pro Asn Asp Lys Tyr Glu Pro Phe
1               5                   10

PLATELET GEL COMPRISING PLATELET-RICH PLASMA, PLATELET ACTIVATOR AND POLYMER

FIELD OF THE INVENTION

This application is based on Italian Patent Application No. RM2004A 000638 filed on Dec. 24, 2004, the content of which is incorporated hereinto by reference.

The present invention relates to a semi-synthetic platelet gel useful for reconstructing muscle and/or bone tissues and a method for the preparation thereof. More particularly, the present invention relates to a semi-synthetic platelet gel comprising platelet-rich plasma, at least one platelet activator, and a biologically acceptable polymer.

STATE OF THE ART

Platelet gels are being used more and more for reconstructing muscle and/or bone tissues instead of fibrin gel, which is also known as fibrin sealant or fibrin glue.

Fibrin gels are two-component systems, comprising a first component containing fibrinogen, a fibrin-stabilizing factor, and fibronectin, and a second component containing thrombin, calcium chloride and a fibrinolysis inhibitor. Fibrin gels can be homologous (from a donor) or autologous (from the patient himself). Homologous gels can have problems of compatibility and of transmission of infections, and are subject to human error. Autologous gels have the drawback that the preparation takes a long time (as much as 3-5 days).

Said platelet gels are used at present in maxillofacial surgery especially for raising the maxillary sinus to make it suitable for an implant, in the treatment of diabetic, vascular and decubitus ulcers, in wound healing after heart surgery and, recently, also in orthopaedics for treating pseudarthrosis, for implanting prostheses and for speeding up the healing of fractures.

Platelet gels differ from fibrin gels in having a higher concentration of platelets and a higher concentration of native fibrinogen.

Various protocols for the preparation of platelet gels are described in the literature. However, the general methodology involves the following steps:
1. Taking of a suitable amount of whole blood from a donor (in the case of homologous gels) or from the patient himself (in the case of autologous gels) and anticoagulation treatment thereof with sodium citrate or citrate phosphate dextrose.
2. Concentration of the platelets and removal of most of the erythrocytes by means of a cell separator or by successive centrifugations according to well-known techniques or by simple sedimentation (E. Sumida et al., IADR/AADR/CADR 82nd General Session, Mar. 10-13, 2004) while avoiding platelet activation. In this way the platelet-rich plasma (PRP) is obtained, with a platelet concentration possibly not below 1 million/µL. 3. Activation of the PRP by adding a calcium salt (e.g. calcium chloride or calcium gluconate), thrombin (human or bovine), batroxobin, or other activators (for example collagen, ADP and serotonin, as described in U.S. Pat. No. 6,322,785) to activate the coagulation process and hence the formation of platelet gel.

In treatments for bone reconstruction, mineral additives of calcium phosphate mixed with particles of bone and bone marrow can then be added to the resultant platelet gel.

Activation of the platelets triggers the process of degranulation of the platelets themselves, which release growth factors, such as PDGF (platelet-derived growth factor), EGF (epidermal growth factor), TGF (transforming growth factor), PDAF (platelet-derived angiogenesis factor), and other factors known in the art and described, for example, in U.S. Pat. No. 5,834,418 and U.S. Pat. No. 6,524,568, and the conversion of fibrinogen into fibrin which undergoes cross-linking and forms the framework for development of the clot. Platelet gel thus exploits the properties of the clot that forms naturally from a wound from which it arose. Platelet gel formation is rapid (even less than an hour).

Despite these advantages, the known platelet gels have some limitations.

The first of these is that the time for clot formation depends on the amount and type of activators added (calcium, thrombin, batroxobin, and the like) and must be estimated empirically.

Another important limitation concerns storage. Thus, whereas PRP can be stored, the clot must only be activated at the moment of use and should be used when it has reached the required consistency for application to the area to be treated or for the procedure that is to be performed. However, as is well known, once the clot has formed the process of retraction begins, reducing its size and making it less and less plastic. Therefore there is only a small time window for use.

Another limitation that is just as important is that during the process of clot retraction there is separation of serum liquid which, of course, contains the growth factors released by the platelets, and therefore, if we are not to lose the beneficial effect of these factors, it is necessary to resort only to procedures that also make it possible to use the serum portion released from the clot.

U.S. Patent Application Publication 2003/0152639 discloses a preparation for use in treating damaged tissue, the isolation thereof comprising the steps of: (a) isolating from the patient an amount of whole blood, treating said whole blood with an anti-coagulant agent, and subjecting said whole blood to a centrifugation process to obtain an amount of platelet-rich plasma; (b) adding to the platelet-rich plasma an effective amount of anticoagulant neutralizing agent and fibrinolysis inhibitor; and (c) suspending the platelet-rich plasma by mixing it with one or more structural matrices from a group consisting of maltodextrin powder, hydroxyethyl cellulose, calcium alginate, carageenan, hydroxyethyl starch, hyaluronic acid, regenerated oxidized cellulose, methyl cellulose, and/or glycerin, to increase viscosity of the platelet-rich plasma and to form a gelatinous preparation; and, (d) subsequently storing said gelatinous preparation in an unactivated state.

According to Section [0019] of 2003/0152639 the preparation disclosed therein is not activated in vitro. It is the injured tissue that begins or initiates a sustainable and natural physiologic activation of the plasma-rich plasma concentrate, not the external and artificial activation products of the prior art. This preparation suffers therefore from the drawback that the extent and the speed of the activation will depend time by time on the physiologically occurring activating agents present on the wound surface.

U.S. Patent Application Publication 2004/0197319 discloses a wound healing composition derived from a low platelet concentration plasma preparation. The composition differs from conventional platelet gel preparations in that the centrifugal conditions under which the low platelet concentration plasma is prepared are less stringent than those for the preparation of platelet rich plasma and platelet concentrates. The platelet concentrations in the composition disclosed by this document is of from 50,000 to 500,000/µl and more preferably about 80,000 to 200,000/μl depending on the patient's baseline platelet level.

SUMMARY OF THE INVENTION

In a first aspect, the present invention provides a semi-synthetic platelet gel comprising platelet-rich plasma, at least one platelet activator, and a biocompatible polymer selected from the group comprising carbomers, polyalkylene glycols, poloxamers, polyesters, polyethers, polyanhydrides, polyacrylates, polyvinyl acetates, polyvinyl pyrrolidones, polysaccharides, and derivatives thereof.

In a second aspect, the present invention provides a method for the preparation of a semi-synthetic platelet gel comprising the steps of:
1. mixing a platelet-rich plasma with at least one platelet activator, and, before clot formation begins,
2. adding the mixture thus obtained to a biocompatible polymer selected from the group comprising carbomers, polyalkylene glycols, poloxamers, polyesters, polyethers, polyanhydrides, polyacrylates, polyvinyl acetates, polyvinyl pyrrolidones, polysaccharides, and derivatives thereof.

The semi-synthetic platelet gel of the present invention overcomes the above mentioned drawbacks in that it does not tend to clot and its rheological properties are considerably stable over time. Furthermore, it has a therapeutic activity at least equal to that of conventional platelet gel.

REFERENCES

1. "Platelet Gel: An autologous alternative to fibrin glue with applications in oral and maxillofacial surgery", Whitman, D. H. et al., J. Oral Maxillofacial Surgery, 1294-1299 (1997).
2. "Platelet-rich plasma: Growth factor enhancement for bone grafts", Marx, R. E. et al., Oral Surg. Oral Med. Oral Pathol. Oral Radiol. Endod., Vol. 85, 638-646, (1998).
3. "Thrombin signalling and protease-activated receptors", Coughlin, S. R., Nature, Vol. 407, 14 Sep. 2000, pages 258-264, Macmillan Magazine Ltd.
4. "Design and evaluation of potent peptide-mimetic PAR1 antagonists", Derian C. K. et al., Drug Development Research 59:355-366 (2003), Wiley-Liss Inc.

DETAILED DESCRIPTION OF THE INVENTION

The expression "platelet-rich plasma" (PRP) means a plasma having a platelet concentration of at least 1 million per microlitre.

The expression "semi-synthetic platelet gel" means the gel of the present invention obtained from a platelet-rich plasma by adding a platelet activator and a synthetic polymer.

The platelet-rich plasma (PRP) for use in the present invention can be prepared according to various procedures known in the art. The procedure described, in "Platelet-rich plasma: Growth factor enhancement for bone grafts", Marx, R. E. et al., Oral Surg. Oral Med. Oral Pathol. Oral Radiol. Endod., Vol. 85, 638-646, (1998), is quite simple and affords good results.

The procedure comprises taking a certain amount of blood from a patient and transferring said blood to a container together with an anticoagulant of the citrate-phosphate-dextrose type. Then the blood is transferred to a centrifuge tube and is centrifuged at approx. 5600 rev/min, thus obtaining separation into a number of layers: a clear top layer of platelet-poor plasma (PPP), a dark bottom layer of erythrocytes, and a middle layer, containing the platelet-rich plasma fraction. The top layer of platelet-poor plasma is removed by suction and the remainder is centrifuged again at 2400 rev/min for further separation of the fractions that remain. Then the middle layer, containing the platelet-rich plasma fraction, is removed and stored at room temperature for later use.

Another method that can be used is described in U.S. Pat. No. 6,398,972 and comprises subjecting the blood taken from a patient to a first centrifugation to separate a dark bottom layer containing red blood cells from a clear top layer consisting of a platelet-enriched plasma, decanting the top layer, and subjecting the same to a second centrifugation to separate a top layer consisting of a platelet-poor plasma (PPP) from a bottom layer of a platelet-rich plasma (PRP). The first centrifugation is performed at approx. 1200 g, i.e. at approx. 3600 rev/min, for a period of time of approx. two minutes, and the second centrifugation is performed preferably at approx. 1000 g, i.e. at approx. 3000 rev/min, for a period of time of approximately eight minutes.

Generally, the term "platelet activator" means a compound that is able to activate the release of platelet growth factors and the conversion of fibrinogen into fibrin. For the purposes of the present invention, the term "platelet activator" means a compound that is able to activate the release of platelet growth factors, but is not capable of forming a clot in less than 15 minutes' time.

The platelet activators for use in the present invention are preferably selected from the group comprising pharmaceutically acceptable calcium salts, for example calcium chloride or calcium gluconate (or their solutions as described in GB 495,675), and peptides capable of activating the thrombin receptor (TRAP—thrombin receptor activating peptide), or mixtures thereof. Several types of TRAP, specific to the various thrombin receptors, are known in the art. Three different thrombin receptors are known in man, named PAR-1, PAR-3 and PAR-4 (PAR: protease activated receptor). The PAR-1 receptor is considered to be the main one responsible for thrombin platelet activation. The known TRAPs have a peptide sequence of from 5 to 14 amino acids. The TRAP preferred according to the present invention corresponds to an amino acid sequence that is unmasked by the action of thrombin on PAR-1. Said sequence corresponds to the peptide sequence Ser-Phe-Leu-Leu-Arg-Asn (SFLLRN) (SEQ ID NO: 1). Other known TRAPs that can be used are SFLLR (TRAP-5) (SEQ ID NO: 2), SFLLRNP (TRAP-7) (SEQ ID NO: 3), SFLLRNPNDKYEPF (TRAP-14) (SEQ ID NO: 4). These TRAPs are also useful in their amide form, i.e. in the form wherein the carboxy terminal group (—COOH) has been converted to an amide group (—CONH$_2$).

The pharmaceutically acceptable calcium salts are added in amounts such as to obtain a calcium concentration in the range of from 1 to 100 millimols per litre of PRP, preferably of from 2 to 50 millimols per litre of PRP. The TRAPs are added in amounts such as to obtain a concentration in the range of from 5 to 500 micromols per litre of PRP, preferably of from 10 to 250 micromols per litre of PRP.

Advantageously, the biocompatible polymers used in the present invention are selected from the group comprising carbomers (acrylic acid polymers crosslinked with a polyalkenyl polyether), polyalkylene glycols (for example, polyethylene glycols and polypropylene glycols), poloxamers (polyoxyethylene-polyoxypropylene block copolymers), polyesters, polyethers, polyanhydrides, polyacrylates, polyvinyl acetates, polyvinyl pyrrolidones, and polysaccharides such as, for example, hyaluronic acid, derivatives of hyaluronic acid, in particular crosslinked hyaluronic acid and esters of hyaluronic acid (for example, benzyl ester of hyaluronic acid), hydroxyalkylcelluloses (for example, hydroxymethylcellulose and hydroxyethylcellulose), and carboxyalkylcelluloses (for example, carboxymethylcellulose).

Preferably, the biocompatible polymers used in the present invention are selected from the group comprising polyethylene glycols, poloxamers, polyvinyl pyrrolidone, hyaluronic acid, benzyl hyaluronate esters, crosslinked hyaluronic acid, hydroxymethylcellulose, hydroxyethylcellulose, and carboxymethylcellulose.

Typically, in the process of this invention the maximum time elapsing between step 1 (i.e. mixing a platelet-rich plasma with at least one platelet activator) and step 2 (i.e. adding a biocompatible polymer) is of 15 minutes, preferably of 10 minutes, still preferably of 5 minutes.

The addition of the biocompatible polymer within such a period of time prevents the formation of a clot and the thus obtained preparation retains the properties of an activated platelet rich plasma over time.

The biocompatible polymer which is added to the PRP/activator mixture may be in the form of a solution or dispersion in water.

Furthermore, said biocompatible polymer may also be in the form of a fibrous dressing or a gel. Advantageously, commercial dressings or fibrous matrices can be used, for example the Hyalofill-F dressing and the Hyaloss matrix, trade names of products composed entirely of an ester of hyaluronic acid with benzyl alcohol (HIAFF™) sold by Fidia Advanced Biopolymers Srl (Italy). An advantageous form of gel is ACP gel, that is an aqueous suspension of microparticles of auto-crosslinked hyaluronic acid at a concentration ranging of from 20 to 60 mg/ml.

In one embodiment, the semi-synthetic platelet gel according to the present invention can contain pharmacologically active substances whose simultaneous action is useful. Typical examples of said pharmacologically active substances are, for example, compounds or products that are able to promote healing (e.g. PDGF, lactoferrin, etc.), which are generally formulated as gels formed from polymeric matrices, disinfectants (e.g. cetylpyridinium chloride, chlorhexidine), antibiotics (e.g. tetracyclines, amphenicols, penicillins, cephalosporins, carbapenemics, sulfamides, macrolides, lincosamides, aminoglycosides, fluoroquinolones, glycopeptides), anti-inflammatory agents and analgesics (e.g. NSAIDs, such as naproxen, diclofenac, ketoprofen, ketorolac, nimesulide, ibuprofen, acetylsalicylic acid, piroxicam, meloxicam, and the like), local anaesthetics (e.g. lidocaine, pramoxine, diclonine, bupivacaine, mepivacaine, quinidine, procainamide, mexiletine, tocainide, benzidamine), opioids (e.g. buprenorphine, codeine, dihydrocodeine, fentanyl, hydrocodone, hydromorphone, methadone, morphine, oxycodone, oxymorphone, pentazocine), anabolic agents (e.g. clostebol, zeranol, danazol).

The method according to the present invention provides a gel that is much more reproducible than the platelet gels known in the art.

In the present invention, an important variable is the platelet concentration in the blood taken from the patient (starting whole blood). The higher the platelet concentration in the starting whole blood, the higher will be the platelet concentration in the PRP.

The viscosity of the semi-synthetic platelet gel of the invention is stable over time without dispersion of growth factors. Advantageously, the viscosity of the semi-synthetic platelet gel of the invention is higher than 3000 cP, preferably in the range of from 4000 cP to 50000 cP, and even more preferably of from 5000 cP to 20000 cP.

The amount of polymer added to the mixture of activated PRP will be such as to obtain the desired level of viscosity. Said amount will range, therefore, depending on the type of polymer used and on the required viscosity of the semi-synthetic platelet gel of the present invention.

Sometimes, the measured values of PDGF-AB released from the platelet gel of the invention in various experimental conditions are lower than those measured in the case of conventional platelet gels. Without limiting in any way the present invention, it has been speculated that this might be due to the ability of some polymers of the present invention to mask the presence of that portion of PDGF-AB that is not measured.

The following examples are provided to illustrate the present invention, without limiting it in any way.

Example A

Platelet-rich Plasma (PRP)

45 ml of venous blood was taken from a patient by means of a syringe containing 5 ml of 0.38% sodium citrate. The whole blood was centrifuged for 20 minutes at 180 g in a swing-arm centrifuge to separate the red blood cells from the platelet plasma. The sediment of red blood cells was drawn through a cannula inserted in the stopper of the centrifuge tube. The platelet plasma was centrifuged again for 15 minutes at 580 g to separate a sediment of platelets from the supernatant platelet-poor plasma (PPP). The supernatant PPP was drawn until approx. 5 ml of a liquid residue was left in the tube. The sediment of platelets was suspended by shacking the liquid residue to obtain the platelet-rich plasma (PRP).

Using this procedure, a PRP was obtained having a platelet concentration greater than 1,000,000 per microlitre.

Comparative Example 1

Platelet Gel

One vial of Botropase (containing 1 IU of batroxobin) was dissolved in 0.5 ml of a 0.2M solution of calcium chloride. The solution obtained was added to 5 ml of PRP prepared according to the method described in the preceding Example A, stirred carefully, and transferred onto a Petri dish, then the clot formation time was measured. The test was repeated three times. Clot formation occurred on average within 10 minutes.

Comparative Example 2

Platelet Gel 50 microlitres of a solution of human thrombin (500 IU per ml) was added to 5 ml of PRP prepared according to the method described in the preceding Example A. The solution obtained was mixed carefully and then transferred onto a Petri dish, then the clot formation time was measured. The test was repeated three times. Clot formation occurred on average within 5 minutes.

Comparative Example 3

Platelet Gel 0.5 ml of a 0.2M solution of calcium chloride was added to 5 ml of PRP prepared according to the method described in the preceding Example A. The solution obtained was mixed carefully and then transferred onto a Petri dish, then the clot formation time was measured. The test was repeated three times. Clot formation occurred on average within 15 minutes.

Example 4

Semi-synthetic Platelet Gel of the Invention 0.5 ml of a 0.2M solution of calcium chloride was added to 5 ml of PRP prepared according to the method described in the preceding Example A. The solution obtained was mixed carefully and then transferred onto a Hyalofill-F dressing (with an area of about 40 cm$^2$) in a Petri dish. Hyalofill-F is the trade-name of a fibrous dressing composed entirely of an ester of hyaluronic acid with benzyl alcohol (HIAFF™) sold by Fidia Advanced Biopolymers SrI.

Absence of clot formation was observed.

Example 5

Semi-synthetic Platelet Gel of the Invention 50 microlitres of a 10 mM solution of TRAP was added to 5 ml of PRP prepared according to the method described in the preceding Example A. The TRAP used was a peptide having a six amino acids sequence SFLLRN. The solution obtained was mixed carefully and then transferred onto a Hyalofill-F dressing (with an area of about 40 cm$^2$) in a Petri dish.

Absence of clot formation was observed.

The values of the PDGF-AB growth factor present in the supernatant of the Petri dish in Examples 4 and 5 were measured at time intervals as shown in Table 1. The values are expressed in pg of PDGF-AB per $10^8$ platelets.

TABLE 1

|  | 30 minutes | 1 hour | 2 hours | 24 hours |
| --- | --- | --- | --- | --- |
| Example 4 | 4300 | 4500 | 4200 | 3500 |
| Example 5 | 6500 | 5000 | 4500 | 5000 |

It was observed that the greater part of release had occurred within one hour in the case of Example 4 (addition of calcium chloride) and within 10-15 minutes in the case of Example 5 (addition of TRAP). These levels then remained substantially stable over the next 24 hours.

Example 6

Semi-synthetic Platelet Gel of the Invention 50 microlitres of TRAP 10 mM was added to 5 ml of PRP. The solution obtained was homogenized thoroughly and added to 15 g of a gel comprising a 1% aqueous solution of Carbomer (grade 980) adjusted to pH 7 by a 10% solution of triethanolamine.

After thorough mixing, the gel was ready to be applied to a wound to be healed.

Its viscosity at 25° C. was approx. 16,000 cP.

Example 7

Semi-synthetic Platelet Gel of the Invention 0.5 ml of a 0.2M solution of calcium chloride was added to 5 ml of PRP. The solution obtained was homogenized thoroughly and added to 15 g of a gel comprising a 20% aqueous solution of polyvinyl pyrrolidone (Kollidon 90 F, BASF).

After thorough mixing, the gel was ready to be applied to a wound to be healed.

Its viscosity at 25° C. was approx. 6,000 cP.

Example 8

Semi-synthetic Platelet Gel of the Invention 50 microlitres of TRAP 10 mM was added to 5 ml of PRP. The solution obtained was homogenized thoroughly and added to 15 g of Regranex® [gel with matrix of carboxymethylcellulose sodium containing 0.01% of becaplermin (rhPDGF)].

After thorough mixing, the gel was ready to be applied to a wound to be healed.

Example 9

Semi-synthetic Platelet Gel of the Invention 50 microlitres of TRAP 10 mM was added to 5 ml of PRP. The solution obtained was homogenized thoroughly and added to 15 g of a gel containing 1% of rhlactoferrin (the gel had been prepared with a matrix of Carbomer (grade 980) at 1% as described in WO 2004/024180).

After thorough mixing, the gel was ready to be applied to a wound to be healed.

Its viscosity at 25° C. was approx. 15,000 cP.

Example 10

Semi-synthetic Platelet Gel of the Invention 50 microlitres of TRAP 10 mM was added to 5 ml of PRP. The solution obtained was homogenized thoroughly and added to 15 g of Voltaren® Emulgel (gel with matrix of Carbomer containing 1.16% of diethylammonium diclofenac).

After thorough mixing, the gel was ready to be applied to a wound to be healed.

Example 11

Semi-synthetic Platelet Gel of the Invention 0.5 ml of a 0.2M solution of calcium chloride was added to 5 ml of PRP. The solution obtained was homogenized thoroughly and added to 15 g of Tantum® gel (gel with matrix of hydroxyethylcellulose containing 5% of benzidamine hydrochloride).

After thorough mixing, the gel was ready to be applied to a wound to be healed.

Example 12

Semi-synthetic Platelet Gel of the Invention 50 microlitres of TRAP 10 mM was added to 5 ml of PRP. The solution obtained was homogenized thoroughly and added to 15 g of gel comprising a 0.3% aqueous solution of hyaluronic acid sodium salt.

After thorough mixing, the gel was ready to be applied to a wound to be healed, directly or after being spread on gauze or on a piece of Hyalofill®-F.

The invention claimed is:

1. A platelet gel obtained from a platelet-rich plasma comprising:
   a platelet-rich plasma containing at least 1 million platelets per microliter of plasma, an amount of at least one platelet activator that activates the release of platelet growth factors, but is not capable of forming a clot in less than 15 minutes, and
   at least one biocompatible polymer selected from the group consisting of carbomers, polyalkylene glycols, poloxamers, polyesters, polyethers, polyanhydrides, polyacrylates, polyvinyl acetates, polyvinyl pyrrolidones, polysaccharides, polyethylene glycols, hyaluronic acid, benzyl hyaluronate esters, crosslinked hyaluronic acid, hydroxymethylcellulose, hydroxyethylcellulose carboxymethylcellulose; and derivatives thereof;
   wherein the platelets in said platelet-rich plasma have been activated to release platelet growth factors by said activator, and
   wherein said biocompatible polymer is mixed with the activated platelets to form said platelet gel before the start of clot formation.

2. The platelet gel according to claim 1, wherein said at least one platelet activator is selected from the group consisting of pharmaceutically acceptable calcium salts and peptides capable of activating a thrombin receptor.

3. The platelet gel according to claim 1, wherein said platelet activator is selected from the group calcium chloride and calcium gluconate.

4. The platelet gel according to claim 1, wherein said at least one platelet activator comprises a peptide capable of activating the thrombin receptor that comprises a peptide sequence of from 6 to 14 amino acids.

5. The platelet gel according to claim 1, wherein said at least one platelet activator comprises a peptide capable of activating the thrombin receptor that comprises the amino acid sequence Ser-Phe-Leu-Leu-Arg-Asn (SEQ ID NO: 1).

6. The platelet gel according to claim 4, wherein said peptide capable of activating the thrombin receptor is in an amide form.

7. The platelet gel according to claim 1, wherein said biocompatible polymer is selected from the group consisting of polyethylene glycols, poloxamers, polyvinyl pyrrolidone, hyaluronic acid, benzyl hyaluronate esters, crosslinked hyaluronic acid, hydroxymethylcellulose, hydroxyethylcellulose and carboxymethylcellulose.

8. The platelet gel according to claim 1, prepared from said biocompatible polymer that is in the form of solution or dispersion in water.

9. The platelet gel according to claim 1, prepared from said biocompatible polymer that is in the form of a dressing or fibrous matrix.

10. The platelet gel according to claim 1, prepared from said biocompatible polymer that is in the form of gel.

11. The platelet gel according to claim 1, further comprising at least one pharmaceutically useful compound.

12. The platelet gel according to claim 11 further comprising at least one pharmaceutically useful compound is selected from the group consisting of healing agents, disinfectants, antibiotics, anti-inflammatory agents, analgesics, local anaesthetics, opioids, and anabolic agents.

13. A gel composition having a viscosity greater than 3,000 cP comprising:

a platelet-rich plasma containing at least 1 million platelets per microliter of plasma, at least one platelet activator in an amount that activates the release of platelet growth factors, but which amount is not capable of forming a clot in the platelet-rich plasma in less than 15 minutes, and at least one biocompatible polymer selected from the group consisting of carbomers, polyalkylene glycols, poloxamers, polyesters, polyethers, polyanhydrides, polyacrylates, polyvinyl acetates, polyvinyl pyrrolidones, polysaccharides, polyethylene glycols, hyaluronic acid, benzyl hyaluronate esters, crosslinked hyaluronic acid, hydroxymethylcellulose, hydroxyethylcellulose carboxymethylcellulose; and derivatives thereof;

wherein the platelets in said platelet-rich plasma are activated platelets that have been activated to release platelet growth factors by said at least one platelet activator and have not formed a clot, and wherein said biocompatible polymer is mixed with the activated platelets to form said platelet gel before the start of clot formation.

14. The gel composition having a viscosity greater than 3,000 cP of claim 13 that is prepared by mixing the platelet-rich plasma with the at least one platelet activator to form a mixture, and then adding the biocompatible polymer to the mixture prior to clot formation.

* * * * *